United States Patent [19]

Clayton et al.

[11] Patent Number: 5,182,216
[45] Date of Patent: Jan. 26, 1993

[54] ASSAYS AND DEVICES THEREFOR

[75] Inventors: Richard A. Clayton, Rushden; Philip Porter, Bedford, both of England

[73] Assignee: Unilever Patent Holdings B.V., Netherlands

[21] Appl. No.: 250,629

[22] PCT Filed: Jan. 20, 1988

[86] PCT No.: PCT/GB88/00036
§ 371 Date: Nov. 22, 1988
§ 102(e) Date: Nov. 22, 1988

[87] PCT Pub. No.: WO88/05539
PCT Pub. Date: Jul. 28, 1988

[30] Foreign Application Priority Data

Jan. 22, 1987 [GB] United Kingdom ............... 8701432

[51] Int. Cl.⁵ ................. G01N 33/543; G01N 33/549
[52] U.S. Cl. ........................ 436/518; 422/56; 422/57; 422/58; 422/60; 422/61; 436/528; 436/535; 436/536; 436/807; 436/810; 436/817; 436/818
[58] Field of Search ........... 436/518, 501, 528, 535, 436/536, 169, 807, 808, 810, 817, 818; 435/7, 810; 422/55, 57, 58, 60, 61

[56] References Cited

U.S. PATENT DOCUMENTS 4,742,011  5/1988  Blake et al. .................. 436/518

FOREIGN PATENT DOCUMENTS 0042755 12/1981 European Pat. Off. .
0164180 12/1985 European Pat. Off. .
0192320  8/1986 European Pat. Off. .
0231830  8/1987 European Pat. Off. .

Primary Examiner—Sam Rosen
Attorney, Agent, or Firm—Cushman, Darby & Cushman

[57] ABSTRACT

In a simultaneous marking specific binding assay for an analyte is a liquid sample, such as urine during pregnancy or fertile period test, wherein the liquid sample is simultaneously incubated with a first specific binding reagent immobilized on a solid phase carrier surface and with a second specific binding reagent dissolved or dispersed in the liquid sample and which bears a label by means of which the result of the assay can be determined, the improvement that prior to the incubation the second specific binding reagent is contained within a layer (2a) of readily soluble or dispersible solid material superimposed on the solid phase carrier surface (2a) on which the first specific binding reagent is immobilized. When the solid material dissolves or disperses in the sample liquid, the labelled reagent is released into the sample liquid at the same time as the immobilized reagent is exposed to the sample, and the close proximity of the two reagents overcomes the "hook effect" when the analyte is in high concentration in the sample. (FIG. 2C).

9 Claims, 1 Drawing Sheet

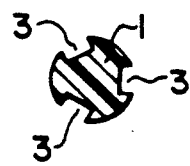
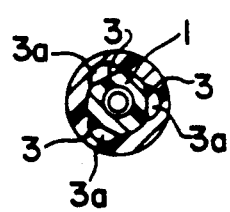
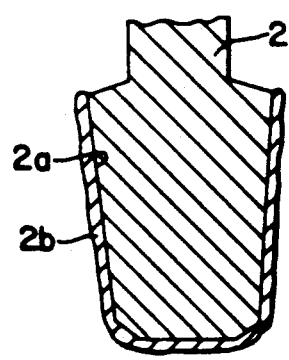
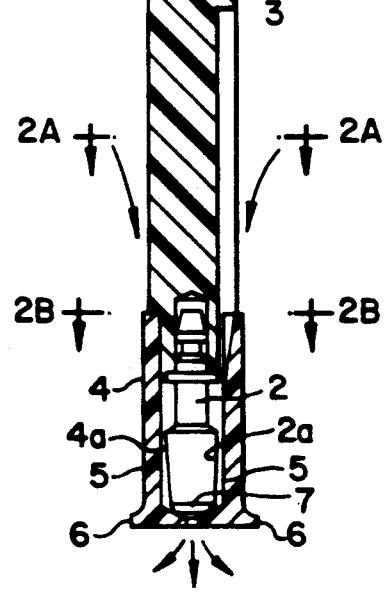
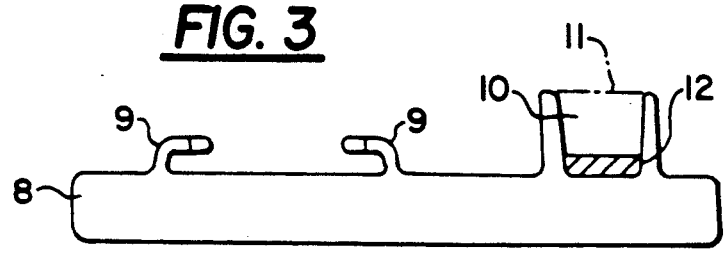

ASSAYS AND DEVICES THEREFOR

The present invention relates to assays and to devices in which such assays can be conducted.

The invention is particularly applicable to assays utilising specific binding, such as immunoassays in which an analyte is assayed by virtue of its participation in a so-called "sandwich" reaction. In a sandwich reaction, the analyte forms a bridge between two reagents which bind specifically with the analyte. Typically one such reagent is fixed to a solid phase, such as a particulate carrier material or to a surface e.g. a peg, and the second reagent is readily soluble or dispersible in a liquid medium (e.g. a medium containing the analyte to be assayed). The second reagent provides a means for determining the extent to which the sandwich binding reaction has taken place. Many examples of such systems are known and used in a wide variety of assay tests. In a very typical example, the second reagent is linked to a chemical marker, such as an enzyme, which is allowed to participate in a chemical reaction following the specific binding step and the chemical reaction produces an observable result, such as a colour change or colour formation.

Conventionally, the sandwich reaction is performed sequentially with the fixed reagent being contacted with the sample, and following an appropriate incubation period to allow the reagent to pick up the analyte, the solid phase is removed from the sample and contacted with the second reagent so that the sandwich reaction can be completed.

A simpler procedure would involve having both of the specific binding reagents present with the sample and permitting the sandwich reaction to take place in a single incubation. One step in the conventional procedure would then be avoided. This simpler procedure, often referred to as simultaneous marking, performs well under most circumstances but can prove unreliable if the sample to be analysed contains a high concentration of the analyte. A phenomenon, known as the "hook effect", then occurs. The high concentration of analyte saturates both of the specific binding reagents and the necessary bridge between the two specific binding reagents is not always formed. When the extent to which the specific binding reaction has occurred is assessed, a spuriously low result is observed because only a proportion of the labelled specific binding reagent has been linked via a single analyte molecule to the specific binding reagent linked to the solid phase. Pregnancy tests in which the analyte is HCG are examples of assays in which the "hook effect" can be a significant problem. There is therefore a need for a simultaneous marking sandwich assay, the reliability of which is independent of the concentration of analyte in the sample. The present invention provides a simultaneous marking assay system wherein a first specific binding reagent immobilised on a solid phase carrier is simultaneously incubated with a liquid sample suspected of containing an analyte to which the binding reagent is specific and with a second binding reagent dissolved or dispersed in the liquid sample bearing a label by means of which an analytical result can be determined and which second binding reagent is also specific for the analyte and which can therefore cooperate with the first binding reagent in a "sandwich" reaction, wherein prior to the incubation the second specific binding reagent is contained within a layer of solid material superimposed on the sensitised surface (i.e. the surface on which the first specific binding reagent is immobilised) of the solid phase, and which material is readily soluble or dispersible in the liquid sample. When the solid phase is contacted with a liquid sample and the solid material layer dissolves or disperses, the entrapped labelled reagent is released into the liquid sample and the immobilised reagent is simultaneously exposed to the liquid sample. The close proximity of the two reagents ensures that there is a high chance of them cooperating in a "sandwich" reaction with any analyte molecules in the sample, even when the analyte is in high concentration. A readily water-soluble sugar, such as sucrose, is an ideal material.

In practice, unless the soluble or dispersible layer is superimposed on the sensitised surface (as distinct from being located on a nearby surface) it tends to exacerbate the "hook effect" problem because it can delay release of the labelled reagent whereas the immobilised reagent is immediately exposed to the high analyte concentration in the sample.

In one embodiment, the invention provides a solid phase device, such as a peg, for use in a specific binding assay and which carries immobilised on a surface thereof a specific binding reagent for an analyte, wherein a labelled specific binding reagent for the same analyte is contained in a layer of soluble or dispersible solid material superimposed on the sensitised surface of the device. This device is preferably part of a liquid sampling device for use in a specific binding assay comprising a test component including a sensitised solid surface, removably mounted in spaced relationship with an accessory solid surface carrrying an accessory component so that, upon contact with or immersion in the liquid which is to provide a test sample, liquid of the sample contacts the sensitised solid surface, and the accessory solid surface acts to retain sample liquid in contact with the sensitised solid surface after any removal of the device from further contact with or immersion in the liquid, wherein superimposed on the sensitised surface is a layer of soluble or dispersible material containing a labelled reagent which can participate in a specific binding "sandwich" reaction with the sensitised surface.

The sampling device preferably comprises part of an assay kit together with means for removing the accessory component from the test component and means for detecting labelled reagent which may have become bound to the sensitised surface of the device. Preferably, the sampling device comprises a handling piece incorporating a sensitised peg, superimposed on which peg is the soluble or displaceable layer containing the labelled reagent, and which sensitised surface is located within a removable shroud which provides the accessory surface, the shroud being interlockable with another component of the test apparatus to facilitate removal of the shroud from the peg, and the other component also incorporating a well into which the peg can be inserted after removal of the shroud, the well containing one or more reagents to develop the label.

The binding reagents are preferably immunoglobulins (antibodies). Preferably such antibodies have high, specific affinities for different epitopes on the analyte. Preferably, the antibodies are so-called paired monoclonal antibodies. The present invention can be performed using solid phases, specific binding reagents, labels and label developing systems which are all standard in the art.

In a further preferred embodiment of the invention, an apparatus for carrying out a test or assay using a liquid sample possibly containing some quantity of an analyte to be tested for, includes a sensitised solid surface superimposed on which is a water-soluble or water-dispersible layer of material containing a reagent which participates in a specific binding sandwich reaction with the sensitised surface, the test component which includes the sensitised solid surface is removably mounted in spaced relationship with an accessory solid surface carried on an accessory body, so that upon contact with or immersion in liquid which is to provide the test sample, liquid of the sample contacts the sensitised solid surface, and the accessory solid surface acts to retain sample liquid (in some embodiments, possibly a definite, consistent, and maybe standardised volume of sample liquid) in contact with the sensitised solid surface after any removal of the apparatus from further contact with or immersion in the liquid. In certain embodiments, the accessory solid surface can be closely spaced from the sensitised surface, and may be so placed that it helps in conducting a flow of sample liquid over the sensitised solid surface, e.g. by capillary action or other effect of surface tension. In other embodiments, the accessory solid surface can take the form of a sample liquid holder such as a cup, which is removably fitted to the test component or to the handle. In use, the test component is later removed from its association with the accessory solid surface, and can be treated further, e.g. by washing and exposure to further reactant.

BRIEF DESCRIPTION OF THE DRAWINGS

The description hereinbelow gives forms and examples of preferred devices according to the invention, for carrying out chemical or clinical testing of liquid samples, for example urine samples, by specific binding assay, such a device comprising a test component (2) which has a sensitised solid surface (2a) carrying an immobilised component of a specific binding pair relevant (2b) to the assay, superimposed upon which surface is the layer of material containing the second specific binding component of the sandwich assay, and a handling piece (1), and in which the improvement comprises a removably mounted accessory component (4) carrying an accessory solid surface (5), which is removably mounted in spaced relationship with the test component (2) bearing the sensitised surface (2a), whereby there is left a space (4a) between the sensitised surface and the removable accessory component (4) to act as a container for sample liquid, so that when the device is contacted with a sample liquid source or immersed in liquid which is to provide the test sample, liquid of the sample can enter the space (4a) to contact the sensitised surface (2a), and the accessory surface (5) acts to retain and contain sample liquid in contact with the sensitised surface (2a) even after removal of the device from further contact with or immersion in the source of sample liquid, the test component (2) being so formed that after removal of the removable accessory component (4) the sensitised surface (2a) is left exposed and accessible to further treatment liquid such as washing liquid and/or reagents. The numerals given in the above statement are intended only for purposes of illustration and explanation but not of limitation, and refer to particular examples of the device as given below and illustrated in the accompanying drawings.

Particular embodiments of the preferred devices of the invention are given by way of example without limitation as follows:

(a) The test component carrying the sensitised solid surface can be a slip, plate, bead, peg or section of hollow body such as tubing, mounted on a handle or other holder.

(b) The accessory solid surface can be of substantially complementary shape to the sensitised solid surface and be removably fixed at a location close to but spaced slightly apart from the sensitised surface; it can be a surface of e.g. a shroud, mesh, cover or plug.

(c) The accessory body can be for example a removable snap-on/snap-off fitment or a frictional sliding fitment on the handle or holder, or on the test component carrying the sensitised solid surface. If desired, the handle or holder can have an ejection device which the user can manipulate to dislodge or demount the accessory body when desired.

In one form of device according to the invention, the accessory body can comprise a body of absorbent liquid-retentive material such as a sponge, to hold sample liquid in contact with the sensitised surface of the test component.

When the test component carrying the sensitised solid surface is fitted to the accessory body carrying the accessory solid surface, they cooperate in such a way that passage is left for entry of sample liquid into the space between the sensitised surface and the accessory surface. Passages can be formed according to convenience either within the handle, within the accessory body carrying the accessory surface, or within the test component, or at the places where any two of these three contact each other. The location of such passage can be chosen at will according to the particular shapes chosen for the rest of the apparatus.

Preferably there is also another passageway provided for air to escape from the surfaces between which the sample liquid is to enter, but the need for this depends on the overall form of the apparatus and passage for liquid entry.

(d) The test component can be removed from its mounting in association with the accessory body, with its accessory solid surface, by pulling off the snap-off or frictional sliding fitment. This can most conveniently be done if the accessory body possesses (in addition to its means for removable connexion to the test component carrying the sensitised solid surface) means for attachment to a test kit base or other component which can be handled easily and used to detach the accessory body from its fitted position in proximity to the test component.

In some instances it may be convenient and desirable to provide the test component carrying the sensitised solid surface as a plug-in fitment to a handle: the test component may be either detachable from the handle or not. Then the test component can be mass-produced to ensure uniformity, without involvement of the handle piece in the manufacturing conditions. Alternatively, the test component can be an integral part of the hande.

In one type of embodiment of the invention which can centre around a sensitised component plug-fitted to a handling-piece, the accessory surface can be that of a sample holder which functions as a cup to hold sample liquid around the sensitised surface of the test component.

The sample holder can have formations (e.g. vanes) allowing it to be push-fitted on to the sensitised component and/or handle. The holder can also be arranged for positive location on a stand or in a further container or handling piece. Then the steps needed to use the device are (a) fill the holder with sample liquid enough to contact the sensitised surface, (b) leave in contact long enough for the needs of the particular test in view, (c) engage the holder with the stand or further container or handling piece, (or otherwise eject or dispose of the sample-liquid holder and its contents), so as (d) to obtain the handle and test component free of the other parts of the apparatus so far used, and (e) then to subject the test component to any further procedures needed by the particular test in view.

It will often be convenient to incorporate the stand or further container or handling piece (or other means to separate the test component from the component carrying the accessory solid surface) as part of the packaging or casing in which the test apparatus is supplied to the user, e.g. as part of the lid or base of such a casing.

Most usually, the sensitised surface of the test component of the apparatus described herein is sensitised by immobilising an antibody or antigen or other component of a specific binding reaction to the surface, in known manner. Such immobilisation methods are now well known and widespread in the literature and in themselves do not constitute the present invention. One preferred method is to adsorb the antibody to a polystyrene surface in known manner. Other suitable methods are described and cited in European Specification No 0 014 530, especially the glutaraldehyde method and the methods described in U.S. Pat. No. 3,817,837 (cols 31-34), and GB Specifications Nos 1 316 990 and 1 485 122-3.

Suitable examples of glutaraldehyde coupling techniques have been available in the literature for a long time, in for example S Avrameas, (1969) Immunochem 6 pp 43 et seq, and in "The Enzyme Linked Immunosorbent Assay (ELISA)" by A Voller, D F Bidwell and A Bartlett, (1979) (published by Dynatech Europe, Guernsey, ISBN 0.906036.01.1).

Since at present the most important application of the devices of the present appears to be for the purpose of pregnancy testing by analysis of female (especially, but not exclusively, human) urine samples, a corresponding suitable material to fix on to the test component surface is antibody to human chorionic gonadotrophin (HCG). Other antibodies which are suitable coupling partners for the purposes of tests of related diagnostic significance are for example anti-luteinising hormone (anti-LH) and anti-prolactin.

The dry layer, superimposed on the sensitised surface, is preferably a sugar glaze, or a thin film layer based on gelatin or other film-former such as polyvinyl alcohol. Materials such as soluble starches and dextrans can also be used. Assays are generally conducted in aqueous media, and so the material should most preferably be readily soluble or dispersible in water. Application of the layer can be achieved easily by, for example, contacting the pre-sensitised solid phase surface with an aqueous solution of the glaze-forming material containing the labelled reagent, e.g. by dipping the solid phase into the solution, and then removing excess solution and drying the residual film of liquid on the solid phase. Such drying should be conducted e.g. by air-drying in a desiccator or by freeze-drying, under mild conditions to ensure that the sensitive reagents are not damaged.

The solution should contain a sufficient concentration of glaze-forming material to provide an effective layer of solid material on the sensitised surface. This concentration will vary depending upon the particular glaze-forming material chosen, and may need to be ascertained by simple experiment. Purely by way of example, for sucrose an ideal concentration will be at least about 1%, and more usually at least about 5%, by weight. It is unlikely that the concentration for sucrose will need to exceed about 20% by weight. For gelatin, much lower concentrations will be suitable, and the ideal concentration will generally lie in the range 0.1 to 1% by weight. In the immunology art, techniques for providing reagents in glazes located on solid surfaces are now standard, and/the novelty of the present invention resides primarily in the location of the glaze rather than in its composition. If desired, the layer of solid material can be built up in a series of applications, with intervening drying steps. The rate of dissolution or dispersion of the solid material layer into the liquid sample during the assay can be controlled by choosing a relatively thin or thick layer, and/or applying a superficial coating of less readily soluble material, e.g. of a polymeric nature, on top of the reagent-containg material layer. In any embodiment, it is advisable that the layer should contain the greatest possible concentration of the labelled specific binding reagents, as this will promote the efficiency of the assay. This is a self-evident precaution, and as those skilled in this particular art will be aware, for any chosen labelled reagent the effective concentration will need to be found by simple experiment.

Preferred embodiments of the invention are described below by way of example only.

EXAMPLE 1

FIGS. 1, 2A, 2B and 2C of the accompanying drawings show a diagrammatic part-section through an embodiment of an apparatus in which the invention can be applied, together with auxiliary cross-sections through lines A—A and B—B in the main section, and an enlarged cross-section (2C) of the sensitised portion of the apparatus.

FIG. 3 shows in diagrammatic part cross-section a base unit for use with the device of FIGS. 1, 2A, 2B and 2C.

Shown in the diagrammatic part-sectional drawings is an apparatus for carrying out immunological tests comprising a handle 1 of plastics material. Into a recess in the lower end of handle 1 is plugged a polystyrene or nylon peg 2 which has been sensitised in known manner with a high-affinity anti-HCG antibody, reacted with the plastics surface in sensitising treatment liquid under sensitising conditions (e.g. those appropriate to a known adsorption or glutaraldehyde method) at a concentration of about 2 micrograms/ millilitre. The part of the peg 2 having a sensitised surface 2a is of the order of 5 millimetre long in a suitable embodiment of this example. Techniques for preparation of immunosorbents are well known in themselves and need be no further described to enable the skilled reader to carry out this invention.

The sensitised portion of peg 2 is coated with a thin layer 2b (seen only in FIG. 2C) of sucrose containing high affinity anti-HCG antibodies conjugated with alkaline phosphatase enzyme as marker.

Handle 1 also has a number of longitudinal grooves 3 therein, to allow passage of sample liquid towards the sensitised part of peg 2. As a frictional sliding fit over the end of handle 1 and over peg 2 there is provided a perforated plastics shroud 4 of which the internal surfaces 5 are substantially complementary in shape to the overall shape of sensitised surfaces of the peg 2. Shroud 4 also in this embodiment has grooves 3a complementary to grooves 3 to allow passage of sample fluid into the centre space within shroud 4. There is no need however for any grooves or the like which may be present on the sensitised part of the peg 2 to be repeated in the surface 5. The space 4a within shroud 4 between surface 5 and surface 2a of peg 2 may be such as to allow of the order of 50 microlitre of liquid, (e.g. up to 100 microlitre) to be held between them. Using these dimensions, this can easily be arranged to be a defined or standard volume of liquid taken up automatically and regulated by surface tension/capillarity when the device is used.

Shroud 4 also carries flanges 6 which allow it to be positively located and locked in place on a holder base 8. Shroud 4 also has a lower perforation 7 to allow escape of air when the assembly of handle 1, peg 2 and shroud 4 is exposed to sample liquid, and sample liquid enters via grooves 3 and 3a to contact peg 2 and surfaces 5. Holder base 8 has flange formations 9 which together with the rest of base 8 form a groove or grooves by which to interlock with and hold shroud 4 as a sliding fit by its flanges 6. Base 8 also has a reagent well 10 fitted with a removable seal 11 to contain further reagent 12 to carry out the test.

In use, the assembly comprising handle 1, peg 2 and shroud 4 is exposed to and contacted with a source of liquid to provide a sample. This may be a sample of serum, or urine, e.g. the lower end of the assembly may be held in a urine stream of a person to be the subject of the test, to collect a sample, which enters into space 4a between the sensitised surface 2a and accessory component 4.

After sample collection, the assembly may be removed from the source and slotted into flanges 9 by means of flanges 6 so that it is held in holder base 8, and allowed to stand to incubate for a specified time chosen to suit the particular reagents involved, so that the sample liquid dissolves the sucrose layer 2b and releases the labelled antibodies, and reacts with the specific binding agent carried by surface 2a. Then the user may pull handle 1 and peg 2 away from the holder, separating test component 2 from accessory component 4, leaving shroud 4 behind. The user can then wash the peg 2 in water or other wash fluid if so instructed according to the nature of the particular test, and dip the peg for a specified time (which may be for example of the order of 5-30 minutes) into reagent well 10. In the present example, when applied to a test for HCG, the well 10 may be provided with a liquid having a content of (e.g. 1 mg/ml) bromochloroindolyl-phosphate (substrate reactable with alkaline phosphatase to yield blue product, under known suitable conditions). According to the content of HCG in the original sample, the liquid in well 11 either develops or fails to develop a blue colouration after incubation. This can be visualised by a colour comparison chart, if desired in the presence of a (possibly inert) background colour (e.g. yellow) to convert the colour development into a change of hue, e.g. from yellow to green. The reagents mentioned hereinabove are all well known per se.

EXAMPLE 2

The following is a description of an experiment demonstrating the effectiveness of the invention. The experiment utilises a peg-based assay essentially as just described under Example 1.

Peg Preparation

Pegs were sensitised by being dipped in 10 μg/ml anti beta human chorionic gonadotropin (HCG) monoclonal antibody in PBSA for two hours at ambient temperature. The sensitised pegs were removed from the reagent solution and placed in PBSA until required.

Conjugate Preparation

A reagent solution was prepared from:

100 μl, 4 mg/ml, anti alpha HCG monoclonal antibody in PBSA.

100 μl, Boehringer alkaline phosphatase enzyme, 10 mg/ml as commercially supplied.

5 μl, 15% monomeric glutaraldehyde in distilled water (Polyscience).

These ingredients were mixed for three minutes at ambient temperature, and the reaction stopped by addition of 6 ml of 5% ovalbumin in 0.05M Tris pH 8.2 buffer, plus 1 mM magnesium chloride, plus 0.1 mM zinc chloride. The conjugate was stored overnight at 4° C. before use.

Coating of Pegs

10% sucrose (W/V) was added to a sample of the conjugate and dissolved.

Pegs were removed from the PBSA storage solution, tapped to remove excess buffer and then dipped into the conjugate solution to a depth covering the sensitised peg tip and left for five minutes. The pegs were removed and dried at 37° C. overnight in an incubator, after which they were stored in the desiccated state at ambient temperature.

Assay

These pegs were tested using a range of standardised HCG samples containing HCG concentrations varying from 0 up to 200,000 mIU/ml, in PBSA/2% bovine serum albumin.

As a series of controls, to simulate a conventional wet assay, sensitised pegs having no sucrose layer were tested using the same range of HCG solutions with the addition of 5 μl of the alkaline phosphatase conjugate solution to 180 μl of the HCG sample.

In each assay, the peg was dipped into the sample for 15 minutes, washed with tap water, and developed in BCIP for 15 minutes. The relative intensities of the resulting blue colouration of the sensitised surface were estimated using a standard laboratory reflectance measuring apparatus. Typical results are given below:

| A. Sucrose-coated pegs HCG concentration (mIU/ml) | Relative colour intensity |
|---|---|
| 0 | 2.33 |
| 100 | 5.10 |
| 1,000 | 11.38 |
| 10,000 | 14.52 |
| 100,000 | 13.03 |
| 200,000 | 12.67 |

| B. Conventional wet assay HCG Concentration (mIU/ml) | Relative colour intensity |
|---|---|
| 0 | 0.65 |
| 100 | 0.50 |
| 1,000 | 10.77 |
| 10,000 | 9.54 |
| 100,000 | 3.55 |
| 200,000 | 2.69 |

These results show that in the assay in accordance with the invention the blue colour, indicative of a positive test result, remained strong even at high (100,000 mIU/ml HCG and above) concentrations.

In the wet assay control, at such high concentrations the "hook effect" gave rise to potentially misleading low colour intensities which could in practice be wrongly interpreted as indicating that only a low HCG concentration is present.

We claim:

1. In a specific binding assay for an analyte in a liquid sample involving the steps of simultaneously incubating the liquid sample with a first specific antibody binding reagent immobilised on a solid phase carrier surface and with a second specific antibody binding reagent dissolved or dispersed in the liquid sample and which bears a label by means of which the result of the assay can be determined, permitting a sandwich reaction to occur during incubation between the antibody binding reagents and the analyte and then detecting the amount of reaction which has occurred, the improvement which involves using, as the second binding reagent, an antibody which is contained within a layer of solid material which is applied as a coating superimposed over the solid carrier surface on which the first specific antibody binding reagent is immobilised, the solid material being readily soluble or dispersible in the liquid sample so that as said solid material dissolves or disperses in the liquid sample, the labelled reagent is released at the same time as the immobilized reagent is exposed to the sample thereby avoiding a spuriously low assay result or hook effect occurring if the analyte is present at high concentration in the sample.

2. A solid phase device which carries immobilised on a surface a specific antibody binding reagent for an analyte, characterised in that a labelled specific antibody binding reagent for the same analyte is contained within a layer of solid material which is applied as a coating superimposed on the surface on which the first specific binding reagent is immobilised, the solid material being readily soluble or dispersible in a liquid suspected of containing the analyte so that as said solid material dissolves or disperses in the liquid sample, the labelled reagent is released at the same time as the immobilised reagent is exposed to the sample thereby avoiding a spuriously low assay result or hook effect occurring if the analyte is present at high concentration in the sample.

3. A solid phase device according to claim 2, characterised in that the solid material is selected from the group consisting of sugars, gelatin, film-forming polymers, starches and dextrans.

4. A solid phase device according to claim 3, characterised in that the solid material is sucrose.

5. A solid phase device according to claim 4, characterised in the specific binding reagents are immunoglobulins.

6. A solid phase device according to claim 5, characterised in that the analyte to which both immunoglobulins are specific is human chorionic gonadotropin or luteinising hormone.

7. A liquid sampling device comprising a first component incorporating a solid surface on which is immobilised a specific antibody binding reagent for an analyte, removably mounted in spaced relationship with an accessory solid surface on an accessory component such that, upon contact with or immersion in a liquid which is to provide a test sample, liquid of the sample contacts the first surface, and the accessory surface acts to retain sample liquid in contact with the first surface after removal of the device from further contact with or immersion in the liquid, characterised in that superimposed on the first surface is a layer of solid material containing a labelled specific antibody binding reagent for the same analyte, the solid material being readily soluble or dispersible in the sample liquid so that as said solid material dissolves or disperses in the liquid sample, the labelled reagent is released at the same time as the immobilized reagent is exposed to the sample thereby avoiding a spuriously low assay result or hook effect occurring if the analyte is present at high concentration in the sample.

8. A liquid sampling device comprising a liquid sampling device as claimed in claim 7, together with means for removing the accessory component from the first component and means for detecting any of the labelled reagent which may have become bound in a sandwich reaction with the immobilised reagent.

9. A liquid sampling device according to claim 8, characterised in that the sampling device comprises a handling piece incorporating a peg on the surface of which is immobilised the specific binding reagent and superimposed on which surface is the layer of solid material containing the labelled specific binding reagent, the peg being located within a removable shroud which provides the accessory surface, the shroud being interlockable with a further component of the test kit to facilitate removal of the shroud from the peg, and the further component also incorporating a well into which the peg can be inserted after removal of the shroud and which well contains one or more reagents to develop the label.

* * * * *